United States Patent [19]

Kerschgens

[11] Patent Number: 4,506,454
[45] Date of Patent: Mar. 26, 1985

[54] APPLIANCE FOR THE TREATMENT OF HAIR AND SCALP

[76] Inventor: Johann J. Kerschgens, Arabellastr.5/1815, 8000 München, Fed. Rep. of Germany, 81

[21] Appl. No.: 438,865

[22] PCT Filed: Jun. 9, 1982

[86] PCT No.: PCT/EP82/00120
§ 371 Date: Oct. 15, 1982
§ 102(e) Date: Oct. 15, 1982

[87] PCT Pub. No.: WO82/04382
PCT Pub. Date: Dec. 23, 1982

[30] Foreign Application Priority Data

Jun. 10, 1981 [DE] Fed. Rep. of Germany ....... 3123008

[51] Int. Cl.³ .............................................. F26B 23/04
[52] U.S. Cl. .............................................. 34/4; 34/39; 34/68; 34/97; 219/347
[58] Field of Search .................. 34/3, 4, 39, 97, 99, 34/100; 219/377, 343, 342, 347

[56] References Cited

U.S. PATENT DOCUMENTS 2,458,901  1/1949  Fields ........................................ 34/3
3,508,338  4/1970  Guhl ........................................ 34/3
4,263,500  4/1981  Springer et al. ........................... 34/4

FOREIGN PATENT DOCUMENTS 939646  2/1956  Fed. Rep. of Germany .

Primary Examiner—Larry I. Schwartz
Attorney, Agent, or Firm—Michael J. Striker

[57] ABSTRACT

An ultraviolet radiator enclosed in an individual housing is formed as an attachment to a motor-driven hair drier. The ultraviolet radiator is mountable on the tubular extension of the hair drier.

13 Claims, 5 Drawing Figures

APPLIANCE FOR THE TREATMENT OF HAIR AND SCALP

BACKGROUND OF THE INVENTION

The invention relates to an appliance for the treatment of hair and scalp.

For the treatment of hair, especially for drying, use is made of driers which are available in a very wide variety of designs. The scalp is activated by hair-lotions, massage etc., to prevent the hair from falling out.

SUMMARY OF THE INVENTION

It is an object of the invention to provide and appliance which will permit drying of the hair and treatment of the scalp "in a single operation", with no need for additional aids such as hair-lotions, massaging, or the like.

This purpose is accomplished by the identifying characteristics of claims 1 to 13.

The inexpensive and compact appliance according to the invention not only dries the hair, but also treats the scalp with UV radiation, UV rays being absorbed into the upper layers of the skin, thus producing local heating. A scalp thus treated activates the roots of the hair, i.e. hair fall-out is reduced and, under certain conditions, the growth of hair is even promoted.

The UV A flurorescence has a stimulating effect, while the UV B (Dorno radiation) reddens the skin and has an anti-rachitic effect. Thus specific biological effects are produced, i.e. vitamin A is formed, the skin is reddened and tanned, and the air is also ionized.

The range of applications according to the invention is therefore not limited to the treatment of the hair and scalp. The appliance may also be used to freshen the air in a room and to form ozone. As regards the scalp, correct metering produces irritation of the skin (possibly with slight reddening) and subsequent pigmentation. Vitamin D is also formed in the skin. Suitable treatment also stimulates sanguification which is highly important to the scalp and is the equivalent of a general increase in function.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENTS

All of the representations are purely diagrammatical; wiring, switches, starters for UV radiators and the like are not shown, since they are all well known and readily available commercially.

Figure 1:
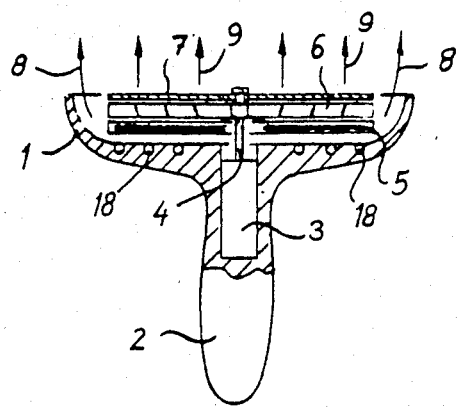
FIG. 1 illustrates an appliance according to the invention, more particularly a very narrow design, suitable above all as a miniature appliance (a disc-like design)

The appliance illustrated in FIG. 1 is more particularly, although not necessarily, flat and in the form of a miniature or travelling appliance. It consists of a housing 1 integral with an electric drive-motor 3 (of miniature design). Drive-shaft 4 runs at least to fan-wheel 6 which it drives (adapted to be switched off if necessary). Also shown is a heating means 18 (a resistance-wire, -rod, or the like). In conjunction with fan-wheel 6, this produces a hair-drier which, although known in principle, is of completely novel design.

UV radiator 5—of an annular design in this case—is preferably located in the position shown, but may also be arranged in front of fan-wheel 6—as seen in the direction of flow indicated by arrow 9. Holders for the UV radiator and the heating means are not shown, since they may be arranged in the housing with known clips or other means of attachment.

During normal operation, air is drawn in the direction opposite to that of arrow 8 and is guided by fan-wheel 6 in the direction of arrow 9. At the same time, UV RADIATOR 5 can be switched on, thus combining drying of the hair with intensive treatment of the scalp (see the preamble to the specification). A cover-disc 7 (adapted to be fitted and removed, to rotate, or to fold like a compur shutter) may be provided. This is made of a suitable material and partly or wholly covers the UV radiator. A disc of this kind may also be perforated, preferably with adjustable openings, in order to obtain the desired metering effect.

However, the appliance may also be used in other ways. For instance, heating-means 18 may be switched off and the heat from UV radiator 5 may be used to dry the hair; or this heat may be used in addition to the heating coils.

It may also be desirable for a UV radiator to be secured to, or incorporated directly into, the inner surface of housing 1 (not shown). It is also possible to reverse the arrangement, i.e. to arrange the UV radiator after heating means 18—as seen in the direction of flow.

According to another configuration of the invention, the inside diameter of housing 1 may be made variable, so that the passage for the air, and also for the UV radiator, may be enlarged or reduced. To this end, cover-rings may be attached to the edge of housing 1.

Figure 2:
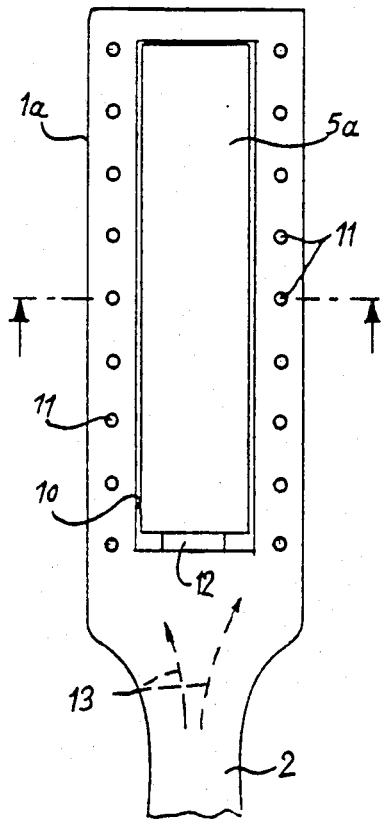
FIG. 2 shows another design in the form of a bar.
Figure 3:
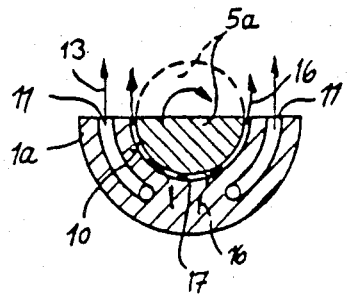
FIG. 3 is a cross-section of FIG. 2.

The foregoing also applies to the design according to FIGS. 2 and 3, in which the appliance is of a more elongated configuration. Handle 2 (not shown) may be used to accommodate an electric motor fan. In this case, hot air flows, in the direction of arrows 13, initially through an annular duct and then through holes 11 to the outside. The central area is occupied by a UV radiator which may be plugged in or mounted rotatably. Guide and retaining means, with stops, known per se are used to achieve total or partial rotation.

Air may be passed through the appliance in the direction of arrow 16; this may require additional holes or merely rearrangement of existing holes. UV radiation may also emerge from the appliance in this direction, if the internal surface of recess 10 is coated with reflecting material. Here again, as described in connection with FIG. 1, UV radiator 5a may be fitted with a covering element, secured, for example, to the wide side (the said element being displaceable, foldable etc.). Appropriate holes are provided to allow the flow of air to emerge in the direction of arrow 13.

Figure 4:
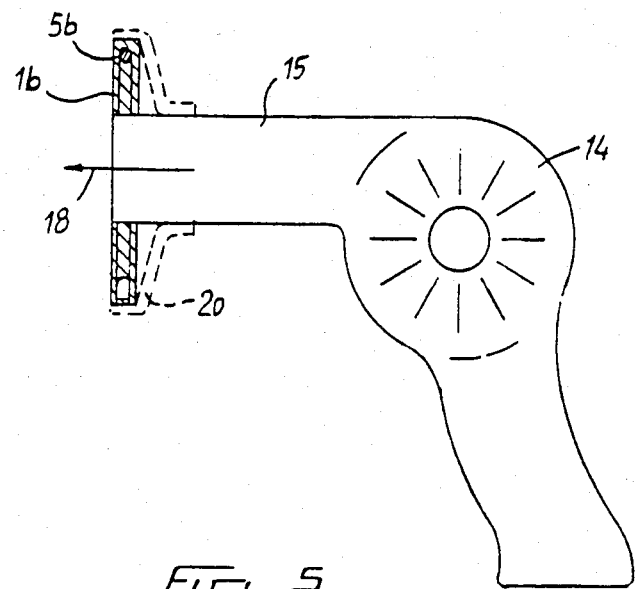
FIG. 4 shows a conventional drier with an attachment containing an UV radiator.
Figure 5:
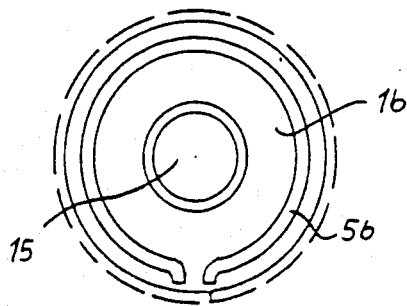
FIG. 5 is a front elevation of the appliance according to FIG. 4.

FIGS. 4 and 5 illustrate a very simple design. In this case, a hair drier 14, known per se, is activated in accordance with the invention, i.e. a UV radiator 5b, preferably accommodated in a housing 1b, is slipped onto the tube of drier 15, to which it is attached by known means—for example, tube 15 of the drier may be externally threaded while the bore of housing 1b may be internally threaded, in which case the UV radiator is simply screwed to the drier. However, the said UV radiator may also be fitted with a rubber sleeve, having a clamping action, which may be slipped onto the drier-tube, making the UV radiator easily removable. Other means of attachment (screwed flanges etc.) are also conceivable. Wiring may be arranged accordingly, or the drier may be fitted with connections for a supply of power.

Shown in dotted lines is a possibly more attractive housing 20 accommodating UV radiator 5b.

It should be pointed out that all of the characteristics shown in connection with individual designs may also be used in a desired combination for the other designs.

Adjustable covers may be fitted to the intake openings in order to control the flow of air. These may be in the form of sliding covers by means of which the inlet-apertures (e.g. slits) may be wholly or partly closed.

The embodiments of the invention in which an exclusive property or privilege is claimed are defined as follows:

1. A hand-held appliance for the treatment of hair and scalp, comprising in combination an electric motor-driven hair drier for applying cold or warm air to a human hair; and ultraviolet radiation means for applying a flow of radiation to a human scalp, said hair drier including a first housing having a tubular extension from which air streams are discharged, said ultraviolet radiation means including a second housing and an ultraviolet radiator enclosed in said second housing, said second housing being removably mountable on said tubular extension and being formed so that air from said drier is allowed to pass therethrough.

2. The appliance as defined in claim 1, wherein said attachment is lockable on said hair drier.

3. The appliance as defined in claim 1, wherein said second housing has an opening adjustable for the mounting on said tubular extension.

4. The appliance as defined in claim 3, further including connecting means for connecting said attachment to said tubular extension.

5. The appliance as defined in claim 4, wherein said connecting means are screws.

6. The appliance as defined in claim 4, wherein said connecting means are of a resilient self-clamping material.

7. The appliance as defined in claim 6, wherein said material is rubber.

8. The appliance as defined in claim 6, wherein said material is plastics.

9. The appliance as defined in claim 3, wherein said opening has a female thread and said tubular extension has a male thread thereon.

10. The appliance as defined in claim 1, wherein said second housing includes reflectors lining an inner surface thereof.

11. The appliance as defined in claim 1, wherein said second housing has air supply passages and includes means for at least partly closing at least some of said air supply passages.

12. The appliance as defined in claim 11, wherein said closing means are slides.

13. The appliance as defined in claim 11, wherein said closing means are compur-like shutters.

* * * * *